United States Patent
Mihalik

(10) Patent No.: US 9,622,806 B2
(45) Date of Patent: Apr. 18, 2017

(54) HEATED ELECTRODES FOR CONTINUED VISUALIZATION OF PULMONARY VEIN POTENTIALS

(71) Applicant: Medtronic CryoCath LP, Toronto (CA)

(72) Inventor: Teresa Ann Mihalik, Montreal (CA)

(73) Assignee: Medtronic CryoCath LP, Toronto, Ontario (CA)

( * ) Notice: Subject to any disclaimer, the term of this patent is extended or adjusted under 35 U.S.C. 154(b) by 433 days.

(21) Appl. No.: 14/157,140

(22) Filed: Jan. 16, 2014

(65) Prior Publication Data

US 2015/0018809 A1 Jan. 15, 2015

Related U.S. Application Data

(63) Continuation-in-part of application No. 13/941,819, filed on Jul. 15, 2013, now Pat. No. 9,345,529.

(51) Int. Cl.
    *A61B 18/02* (2006.01)
    *A61B 18/00* (2006.01)

(52) U.S. Cl.
    CPC ...... *A61B 18/02* (2013.01); *A61B 2018/0022* (2013.01); *A61B 2018/00041* (2013.01);
(Continued)

(58) Field of Classification Search
    CPC .......... A61B 18/02; A61B 2018/00041; A61B 2018/0022; A61B 2018/00375;
(Continued)

(56) References Cited

U.S. PATENT DOCUMENTS

| 5,423,807 A | 6/1995 | Milder |
|---|---|---|
| 6,939,338 B2 | 9/2005 | Waldhauser et al. |

(Continued)

FOREIGN PATENT DOCUMENTS

WO      0141664 A1    6/2001

OTHER PUBLICATIONS

International Search Report and Written Opinion dated Jul. 22, 2014 for International Application Serial No. PCT/CA2014/000497, International Filing Date: Jun. 12, 2014 consisting of 7 pages.

*Primary Examiner* — Michael Peffley
*Assistant Examiner* — Khadijeh Vahdat
(74) *Attorney, Agent, or Firm* — Christopher & Weisberg, P.A.

(57) ABSTRACT

A method and system for cryotreatment and mapping of target tissue. The cryotreatment system may include a cryotreatment catheter, a mapping catheter including one or more mapping electrodes, and one or more temperature sensors located on the mapping catheter and/or the cryotreatment catheter. The cryotreatment catheter distal tip may be short enough to allow at least one mapping electrode to be positioned proximate the cryoballoon, for example, within 6 mm or less from the cryoballoon. Energy, such as radiofrequency energy, may be delivered to one or more mapping electrodes when one or more temperature sensors indicate a temperature of approximately 0° C. or below at one or more mapping electrode in order to thaw or prevent the formation of ice on the mapping electrodes when positioned proximate a cryoballoon during a cryotreatment procedure in order to recapture cardiac signals.

19 Claims, 11 Drawing Sheets

(52) U.S. Cl.
CPC ........... *A61B 2018/00375* (2013.01); *A61B 2018/00714* (2013.01); *A61B 2018/00839* (2013.01); *A61B 2018/0212* (2013.01)

(58) Field of Classification Search
CPC  A61B 2018/00714; A61B 2018/00839; A61B 2018/0212
USPC .................................................. 606/20–26
See application file for complete search history.

(56) References Cited

U.S. PATENT DOCUMENTS

| | | |
|---|---|---|
| 7,255,693 B1 | 8/2007 | Johnston et al. |
| 2003/0176810 A1 | 9/2003 | Maahs et al. |
| 2006/0135953 A1 | 6/2006 | Kania et al. |
| 2007/0276360 A1 | 11/2007 | Johnston et al. |
| 2011/0184274 A1 | 7/2011 | Rosenberg et al. |
| 2012/0150107 A1 | 6/2012 | Cheung et al. |

HEATED ELECTRODES FOR CONTINUED VISUALIZATION OF PULMONARY VEIN POTENTIALS

CROSS-REFERENCE TO RELATED APPLICATION

This application is continuation-in-part of and claims priority to patent application Ser. No. 13/941,819, filed Jul. 15, 2013, entitled MAPPING WIRE WITH HEATING ELEMENT TO ALLOW AXIAL MOVEMENT DURING CRYOBALLOON ABLATION, now patented as U.S. Pat. No. 9,345,529, issued May 24, 2016, the entirety of which is incorporated herein by reference.

STATEMENT REGARDING FEDERALLY SPONSORED RESEARCH OR DEVELOPMENT n/a

FIELD OF THE INVENTION

The present invention relates to a method and system for a heatable mapping cryotreatment catheter that includes heating elements to allow for axial movement of the mapping cryotreatment catheter through a lumen of a medical cryotreatment catheter during a cryoablation procedure and/or includes heating elements that thaw or prevent the formation of ice on mapping elements of the mapping catheter.

BACKGROUND OF THE INVENTION

A cardiac arrhythmia is a condition in which the heart's normal rhythm is disrupted. There are many types of cardiac arrhythmias, including supraventricular arrhythmias that begin above the ventricles (such as premature atrial contractions, atrial flutter, accessory pathway tachycardias, atrial fibrillation, and AV nodal reentrant tachycardia), ventricular arrhythmias that begin in the lower chambers of the heart (such as premature ventricular contractions, ventricular tachycardia, ventricular fibrillation, and long QT syndrome), and bradyarrhythmias that involve slow heart rhythms and may arise from disease in the heart's conduction system.

Certain types of cardiac arrhythmias, including ventricular tachycardia and atrial fibrillation, may be treated by ablation (for example, radiofrequency (RF) ablation, cryoablation, ultrasound ablation, laser ablation, microwave ablation, and the like), either endocardially or epicardially. For example, atrial fibrillation (AF) is frequently treated with pulmonary vein ablation (also called pulmonary vein antrum isolation, or PVAI), a procedure that may involve inserting a mapping cryotreatment catheter through the left atrium of the patient's heart to the pulmonary vein (PV) ostium to map electrical impulses or potentials at the PV ostium before and/or after cryoablation. There is a depth within the PV at which electrical impulses are absent (such a location may be referred to as being "deep" within the PV), with the strength and/or prevalence of electrical impulses being greater closer to the PV ostium. The mapping catheter then may be inserted into the PV before ablation to act as an anchor to a cryoablation element and to support the cryoablation element during positioning at the left atrium/pulmonary vein (LA-PV) junction. Once the mapping catheter is properly seated within the PV, an ablation element (such as a cryoballoon or other ablation catheter configured to be advanced over a wire) is advanced over the mapping catheter until it is in contact with the ostium of the PV, within the left atrium. Proper contact between the cryoballoon and the PV ostium, which results in PV occlusion, may be confirmed using visualization techniques such as fluoroscopy.

Once the cryoballoon is in good position, the mapping catheter is slowly pulled back from deep within the PV to an area closer to the PV ostium. It is desirable to position the mapping catheter as close to the cryoballoon as possible, as the mapping catheter at this location may offer the best chance of contact with tissue that has electrical activity and thus detection and recordation of pulmonary vein potentials (PVPs). Recording these PVPs may provide insight as to the time-to-effect during onset of ablation. Additionally, mapping tissue far distal to the cryoballoon may not provide accurate data about the target isolation site and the effectiveness of cryotreatment and may pick up far field electrical signals that could interfere with the ability of the user to decipher or interpret the signals. Although it is desirable to collect this additional data, users are often forced to leave the mapping catheter deep within the PV during the cryotreatment procedure (for example, cryoablation). This is because, in some cases, retraction of the mapping catheter once the cryoballoon is in place reduces or eliminates the support provided to the cryoballoon by the mapping catheter, and the cryoballoon may slip out of place (that is, occlusion of the PV may be compromised). In those cases, the user must re-advance the mapping catheter to a more distal location within the vein and reposition the cryoballoon. Further, repositioning the cryoballoon typically involves reassessing PV occlusion, such as by the injection of a contrast medium from the cryoballon lumen (such as a guide wire lumen, within which the mapping catheter is slidably disposed) and imaging by fluoroscopy. The use of contrast medium and fluoroscopy not only exposes the patient and clinicians to radiation, but is sometimes poorly tolerated by some patients, including those with renal insufficiency.

During the cryotreatment procedure (for example, cryoablation), refrigerant circulating through the cryoballoon absorbs heat from surrounding tissue. As the tissue freezes, blood adjacent the treatment site may also freeze, creating an "ice ball" that temporarily adheres the cryoballoon to the tissue at the treatment site, a phenomenon called cryoadhesion. Once cryoadhesion occurs, retraction of the mapping catheter from within the PV has less of an effect on cryoballoon stability and could, in theory, be withdrawn and used to detect and record PVPs proximate the ablation site. However, within about ten seconds from commencement of the cryotreatment procedure, fluids within the guide wire lumen around the mapping catheter freeze, effectively locking the mapping catheter in place and preventing its axial movement. Although some currently known methods may involve retraction of the mapping catheter before the onset of freezing (that is, within the first approximately ten seconds), there are several drawbacks to this method. For example, cryoadhesion between the cryoballoon and the tissue may not yet have occurred, and movement of the mapping catheter without cryoadhesion will unseat the cryoballoon and require repositioning of the cryotreatment device.

It is desirable, therefore, to provide a system and device that allows for the axial movement of the mapping catheter during all stages of cryotreatment so that the mapping catheter may not only map LA-PV tissue before and after cryotreatment and anchor the cryoballoon against the PV ostium, but also allow for mapping of the PV tissue proximate the PV ostium during cryotreatment as well. Further, even when the mapping catheter is positionable proximate the cryoballoon, the local temperature may cause ice formation on one or more of the mapping electrodes of the mapping catheter, resulting in attenuation or loss of signal. Therefore, it is further desirable to provide a system and device that prevents or thaws ice formation on mapping catheter electrodes positioned proximate a cryoballoon during a cryotreatment procedure.

SUMMARY OF THE INVENTION

The present invention advantageously provides a method and system for mapping electrical signals within myocardial tissue. In one embodiment, the system includes one or more mapping electrodes on a mapping catheter, an energy source in communication with each of the one or more of the mapping electrodes, and a processor in communication with one or more temperature sensors, the processor being configured to control the energy source to deliver non-ablative energy to the one or more mapping electrodes when the processor determines that the temperature of the one or more mapping electrodes is below a threshold temperature, the determination being based at least in part on temperature signals received from the one or more temperature sensors. The system may further include a treatment catheter including an expandable element and an elongate body including a lumen, the mapping catheter being slidably disposed within the lumen of the treatment catheter elongate body. The one or more mapping elements may be in direct communication with the one or more temperature sensors, for example, if the one or more temperature sensors are located at other locations on the treatment device and/or the mapping device, or the one or more mapping elements may include (for example, be coupled to or integrated with) the one or more temperature sensors. The treatment device may include a distal tip located distal of the expandable element. For example, the one or more temperature sensors may be located on an outer surface and/or an inner surface of the expandable element and/or on the treatment device distal tip. The distal tip may be between approximately 0 mm and approximately 13 mm. The treatment device may further include a guidewire lumen, and the expandable element may include a proximal neck and a distal neck. In one non-limiting embodiment, the distal neck may be turned inward and coupled to a distal portion of the guidewire lumen within the cryoballoon, the expandable element defining a distal face that is coterminous with the guidewire lumen. Further, at least one of the one or more mapping electrodes may be positionable between 0 mm and 2 mm of the expandable element when the at least one mapping electrode is mapping electrical signals within myocardial tissue. The expandable element may be in fluid communication with a source of coolant, and the threshold temperature may be approximately 0° C.

In another embodiment the system may include a cryotreatment device including a first elongate body and a cryoballoon, a mapping device including a second elongate body, the second elongate body being disposable within the guide wire lumen of the first elongate body, a plurality of mapping elements on a distal portion of the second elongate body, a plurality of temperature sensors on at least one of the cryotreatment device and the mapping device, a radiofrequency energy generator in communication with the plurality of mapping elements, and a processor in communication with the plurality of temperature sensors and the radiofrequency energy generator. The processor may be configured to control the energy generator to deliver non-ablative energy to the one or more mapping electrodes when the processor determines that the temperature of the one or more mapping electrodes is approximately 0° C., the determination being based at least in part on temperature signals received from the one or more temperature sensors. The cryotreatment device may further include a distal tip. The distal tip may define a length of between approximately 0 mm and approximately 3 mm. For example, at least one of the plurality of mapping elements may be positionable within approximately 3 mm of the cryoballoon when the at least one mapping element is in contact with an area of target tissue.

The method of performing a cryotreatment procedure may include positioning a mapping device having at least one mapping electrode within a pulmonary vein, positioning a cryoballoon of a cryotreatment device at the pulmonary vein ostium, activating the cryoballoon to ablate adjacent tissue, and transmitting non-ablation energy to the at least one mapping electrode when the temperature at the at least one mapping electrode falls below a threshold temperature. The mapping device may include at least one temperature sensor in direct communication with the at least one mapping element, the non-ablation energy being transmitted to the at least one mapping electrode when the at least one temperature sensor detects a temperature of approximately 0° C. or below. The cryotreatment device may include at least one temperature sensor, the non-ablation energy being transmitted to the at least one mapping electrode when the at least one temperature sensor detects a temperature of approximately 0° C. or below.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
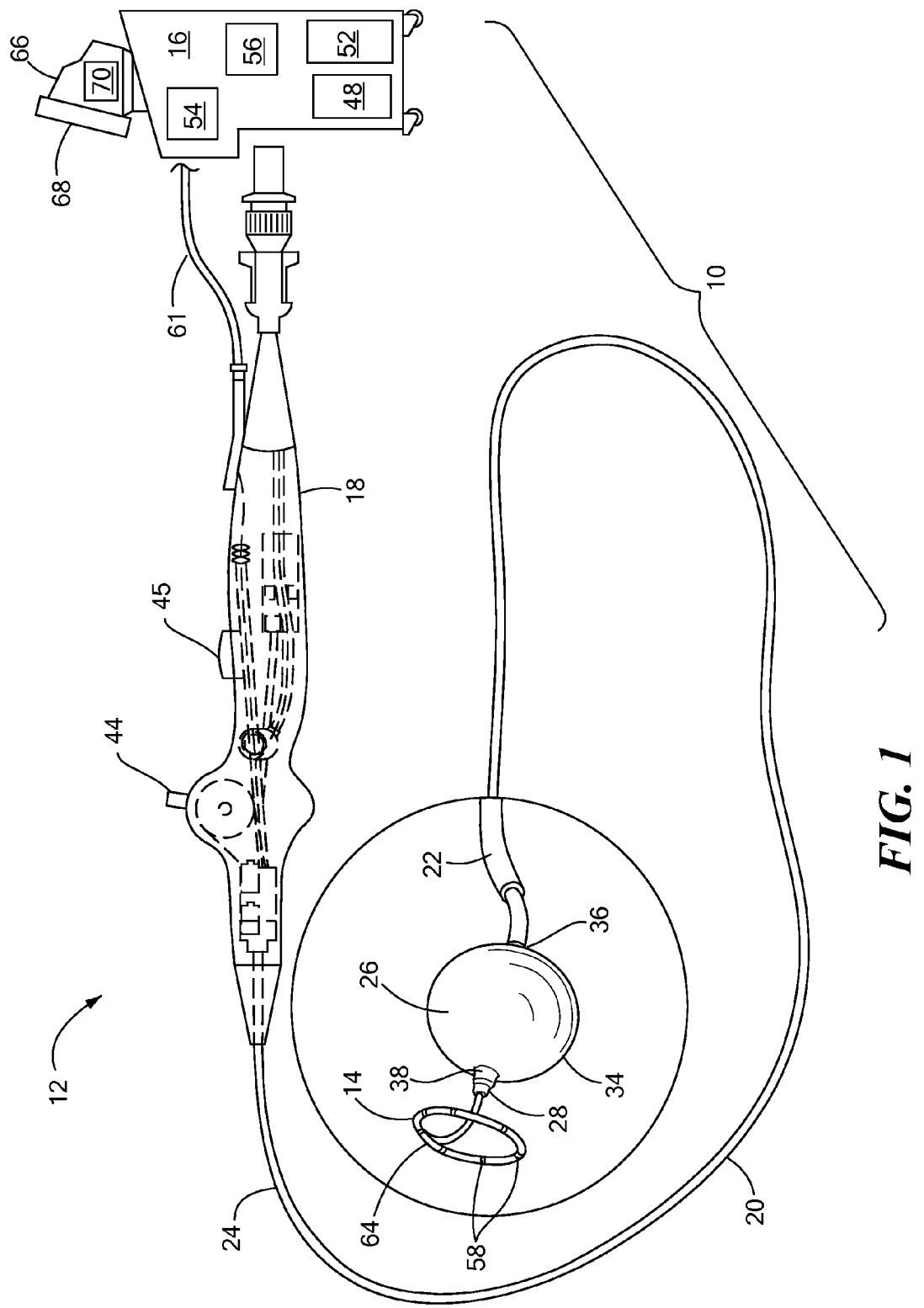
FIG. 1 shows an exemplary system including a cryotreatment catheter and a heatable mapping catheter.

Referring now to FIG. 1, an exemplary system in accordance with the present invention is shown. The system 10 may generally include a cryotreatment catheter 12 for thermally treating an area of tissue, a mapping catheter 14 for sensing and recording electrical signals from tissue (for example, cardiac tissue), and a console 16 that houses various system 10 controls. The system 10 may be adapted for a cryotreatment procedure, such as cryoablation. The system 10 may additionally be adapted for radiofrequency (RF) ablation and/or phased RF ablation, ultrasound ablation, laser ablation, microwave ablation, hot balloon ablation, or other ablation methods or combinations thereof. In any embodiment, however, the cryotreatment catheter 12 will be configured to accept a mapping catheter 14 therethrough. For example, the cryotreatment catheter 12 will include a guide wire lumen or central lumen through which a mapping catheter may be passed, as described in greater detail below.

The cryotreatment catheter 12 may generally include a handle 18, an elongate body 20 having a distal portion 22 and a proximal portion 24, one or more treatment elements 26, a guide wire lumen 28, and one or more sensors 30, 31 (for example, temperature or pressure sensors). Further, the cryotreatment catheter 12 may have a longitudinal axis 32. The treatment element 26 may be a cryoballoon 34, as shown in FIGS. 1-6. The cryoballoon 34 may be coupled to the distal portion 22 of the elongate body 18 of the cryotreatment catheter 12. For example, the cryoballoon 34 may define a proximal portion or neck 36 that is affixed to or coupled to the distal portion 22 of the elongate body 18, and may further define a distal portion or neck 38 that is affixed to or coupled to the guide wire lumen 28 (such as the distal portion 40 of the guide wire lumen 28). The guide wire lumen 28 may lie along the longitudinal axis 28 and be longitudinally movable within the elongate body 18. In this manner, longitudinal movement of the guide wire lumen 28 will affect the shape of the cryoballoon 34, at least when the cryoballoon 34 is inflated. The proximal portion of the guide wire lumen 28 may be in mechanical communication with one or more steering mechanisms 44 in the handle 18 of the cryotreatment catheter 12, such that the guide wire lumen 28 may be longitudinally extended or retracted using one or more steering mechanisms 44, such as knobs, levers, wheels, pull cords, and the like. For example, a longitudinal extender 45 may be included in the handle to advance and retract the mapping catheter 14 within the guide wire lumen 28.

Figure 2:
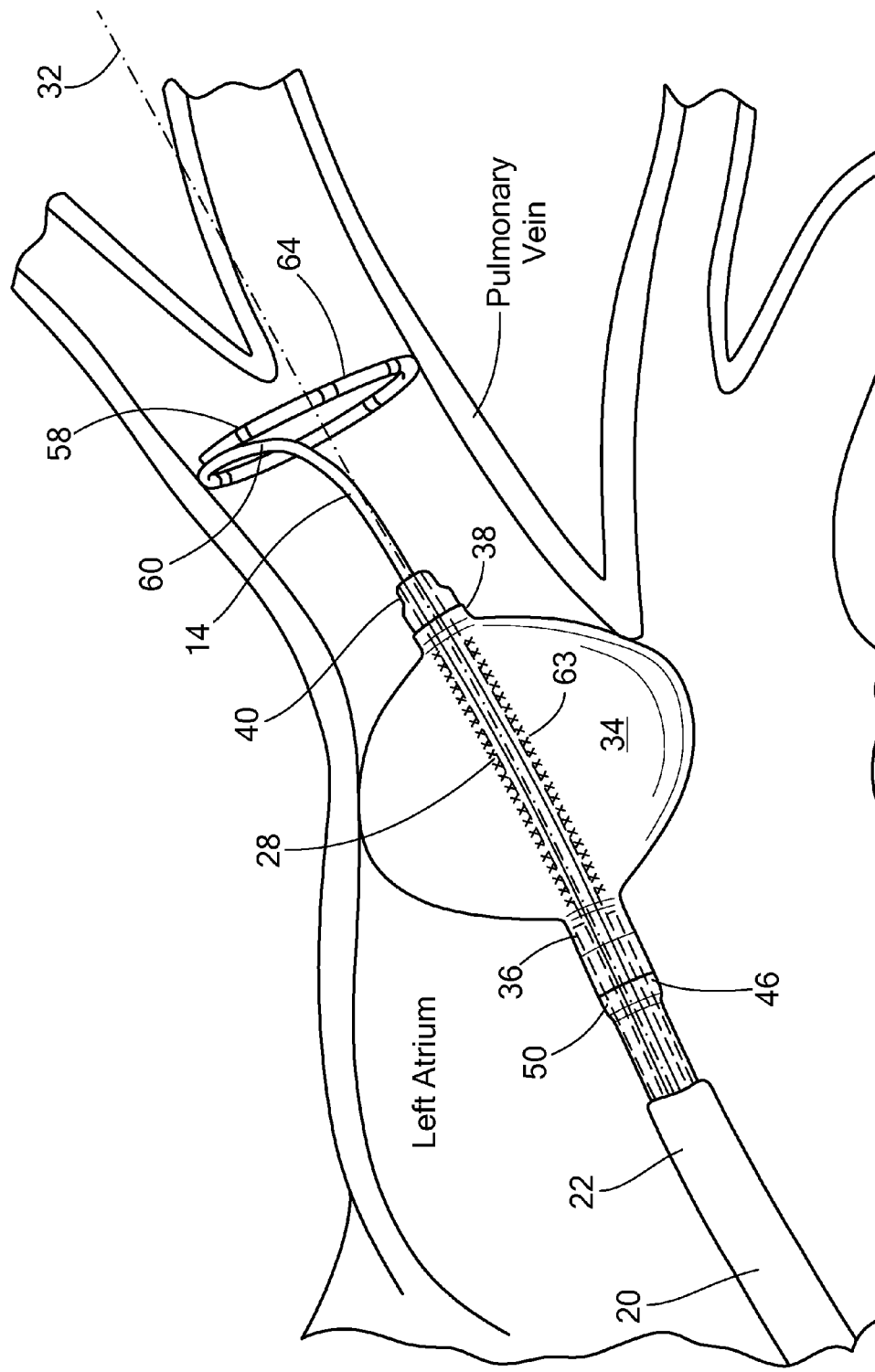
FIG. 2 shows a first view of an exemplary cryotreatment catheter with a heatable mapping catheter, the heatable mapping catheter being extended within the pulmonary vein.
Figure 4:
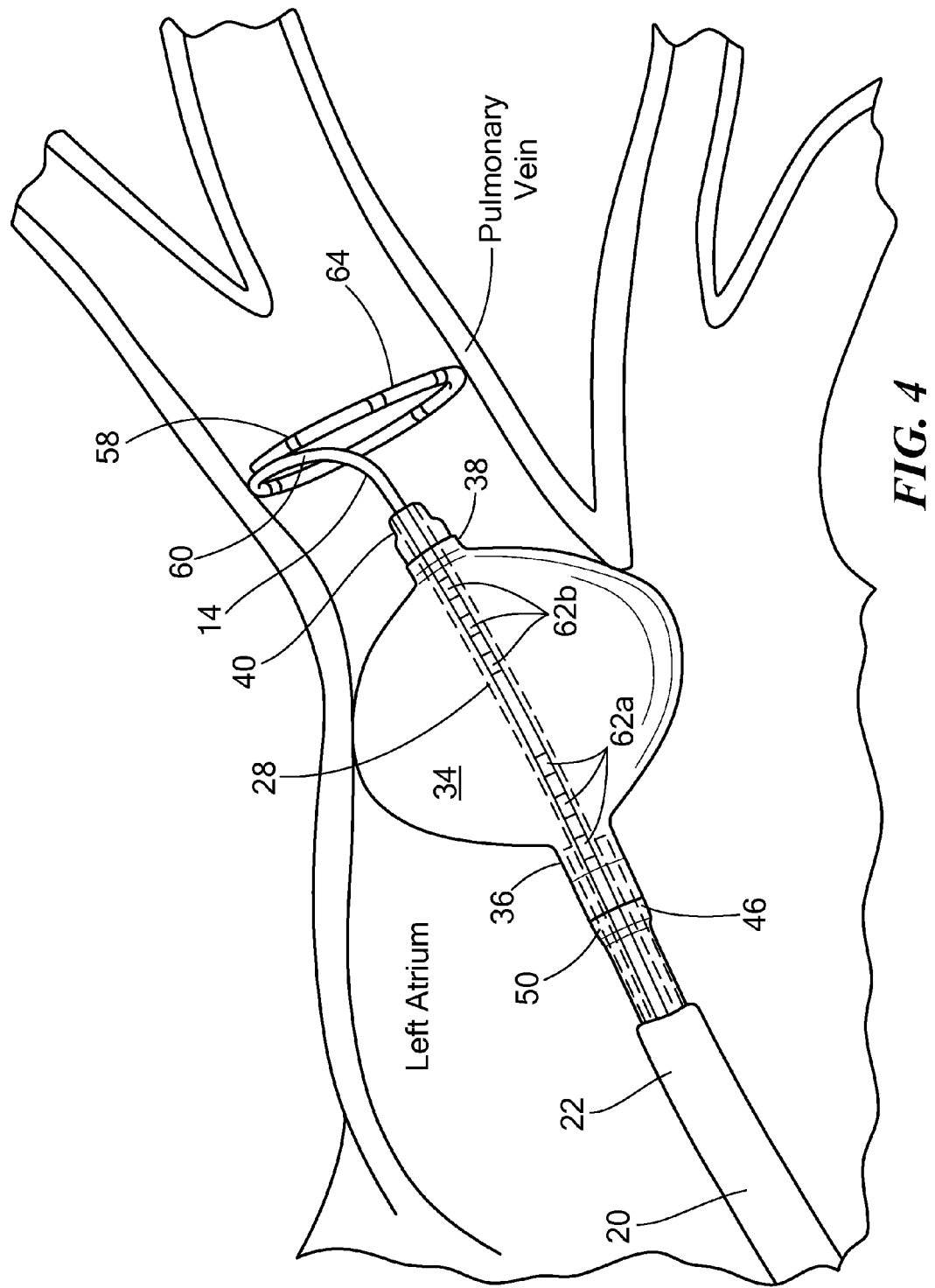
FIG. 4 shows a second view of an exemplary cryotreatment catheter with a heatable mapping catheter, the heatable mapping catheter being retracted proximate the site of cryotreatment.

In addition to the guide wire lumen 28, the cryotreatment catheter 12 may include one or more lumens. As shown in FIGS. 1, 2, and 4, the cryotreatment catheter 12 may include a fluid injection lumen 46 in fluid communication with a fluid supply reservoir 48, and a fluid recovery lumen 50 in fluid communication with a fluid recovery reservoir 52. Further, the fluid recovery lumen 50 may be in communication with a vacuum 54 to facilitate removal of fluid from the cryoballoon 34 (for example, expanded coolant). If the cryotreatment catheter 12 includes thermoelectric cooling elements or electrodes capable of transmitting radiofrequency (RF), ultrasound, microwave, electroporation energy, or the like, the elongate body 18 may include a lumen in electrical communication with an energy generator 56.

The mapping catheter 14 may include an elongate body that is passable (longitudinally movable) through the guide wire lumen 28 of the cryotreatment catheter 12. The mapping catheter 14 may include one or more pairs of mapping elements 58, such as electrodes capable of sensing and recording electrograms from cardiac tissue. The one or more pairs of mapping elements 58 may be disposed along a distal portion 60 of the mapping catheter 14. Further, the one or more pairs of mapping elements 58 may be composed of metal or other electrically conductive material and may be affixed on an outer surface of the mapping catheter 14, integrated and flush with the body of the mapping catheter 14 (such that the mapping catheter has a smooth outer surface), may be areas of exposed electrically conductive material (for example, where an outer insulative layer has been removed), or may be otherwise affixed or coupled to or integrated with the mapping catheter 14.

As is shown and described in more detail in FIGS. 2-5, in one embodiment, the mapping catheter 14 may further include one or more heating elements 62. For example, the one or more heating elements 62 may be located on the mapping catheter 14 such that the one or more heating elements 62 are positioned within the guide wire lumen 28 when the mapping catheter 14 is extended and when it is retracted. The mapping catheter 14 may be deformable from a first substantially linear configuration and a second circular or lasso-type configuration. For example, the mapping catheter 14 may be composed of a shape memory material, with the neutral configuration being the lasso-type configuration. Passing the mapping catheter 14 through the guidewire lumen 28 may bias the mapping catheter 14 to assume the substantially linear configuration, but as the distal portion of the mapping catheter 14 exits the guidewire lumen 28, the distal portion may again assume the neutral lasso-type configuration.

The console 16 may be in electrical and fluid communication with the cryotreatment catheter 12 and the mapping catheter 14, and may include one or more fluid (for example, cryotreatment coolant) reservoirs 48, fluid return reservoirs 52, energy generators 56, and computers 66 with displays 68, and may further include various other displays, screens, user input controls, keyboards, buttons, valves, conduits, connectors, power sources, processors, and computers for adjusting and monitoring system 10 parameters. The computer 66 may include one or more processors 70 that are in electrical communication with the one or more pairs of mapping elements 58, the one or more sensors 30, the one or more heating elements 62, and the one or more treatment elements 26 and programmable to execute an algorithm for locating one or more optimal treatment areas, for controlling the temperature of the one or more treatment elements 26, and/or for regulating the operation of the one or more heating elements 62. As a non-limiting embodiment, the proximal portion 61 of the mapping catheter 14 may include an electrical connection that is matable to at least a portion of the console (for example, with the electrophysiology recording equipment) and in electrical communication with the one or more processors 70.

Referring now to FIGS. 2-5, an exemplary cryoablation catheter with a heatable mapping catheter is shown, the heatable mapping catheter being extended within the pulmonary vein. As shown and described in FIG. 1, the mapping catheter 14 may be longitudinally movable within the guide wire lumen 28, so that the mapping catheter 14 may be extended and retracted relative to the cryotreatment catheter 12. For example, the mapping catheter 14 may be extended such that the distal portion 60 is located deep within the PV to anchor the cryotreatment catheter 12 as the cryoballoon 34 is seated at the PV ostium and cryotreatment initiated. When the distal portion 60 of the mapping catheter 14 is positioned deep within the PV, electrical signals from the tissue may not be present, and therefore not recorded by the one or more pairs of mapping elements 58. Before cryotreatment is initiated, the mapping catheter 14 may be partially retracted to a position within the PV that is closer to the PV ostium where electrical signals may be present, such that at least one pair of mapping elements 58 may detect and record PVPs. Further, once the cryoballoon 34 reaches temperatures low enough to cause cryoadhesion between the cryoballoon 34 and the tissue with which the cryoballoon 34 is in contact, the mapping catheter 14 may be further retracted (that is, pulled through the guide wire lumen 28 toward the proximal portion 24 of the elongate body 18) to bring the one or more pairs of mapping elements 58 of the mapping catheter 14 even closer to the cryotreatment site, where electrical signals are stronger and/or more prevalent, for further mapping.

In present systems, when the cryoballoon 34 is cold enough to cause cryoadhesion with adjacent tissue, the cryoballoon 34 is also cold enough to freeze fluids within the guide wire lumen 28, effectively locking the mapping catheter 14 in the extended position. That is, fluids (for example, contrast medium ejected from the guide wire lumen 28 to assess occlusion of the PV ostium by the cryoballoon 34) may freeze within the guide wire lumen 28 and prevent the longitudinal movement of the mapping catheter 14, a phenomenon that usually occurs after approximately 10 seconds from the onset of a cryotreatment procedure, such as cryoablation. In contrast, the one or more heating elements 62 on the mapping catheter 14 may be activated to heat the fluid within the guide wire lumen 28 to a temperature sufficient to melt the frozen fluid or prevent the fluid from freezing, so that the mapping catheter 14 may freely move within the guide wire lumen 28 during all stages of cryotreatment.

A second benefit of having unfrozen fluids within the guide wire lumen 28 is that occlusion assessment of the cryoballoon using the pressure wedge monitoring technique may continue to provide information to the user during the onset of ablation. The pressure wedge monitoring technique is a way to evaluate occlusion without requiring exposure to radiation for the patient and staff. It may be especially useful for patients with renal insufficiency and patients who do not tolerate contrast media. In present systems, fluids within the guide wire lumen 28 freeze within about 10 seconds from the onset of cryotreatment, and pressure readings disappear. This is because the pressure wedge monitoring technique requires the presence of a column of fluid within the cryotreatment device. When the liquid is frozen, the pressure cannot be determined using this method. Thus, there is no information about any loss of position of the cryoballoon 34 unless another technique is used to monitor occlusion. However, fluoroscopy is also nearly impossible to use for assessing cryoballoon 34 position, because the contrast medium cannot be ejected from the cryotreatment catheter 12 through the frozen liquid within the guide wire lumen 28. A technique such as Doppler flow using intravascular ultrasound could be used to assess cryoballoon 34 position; however, such systems are costly and do not always produce satisfactory results.

Figure 3:
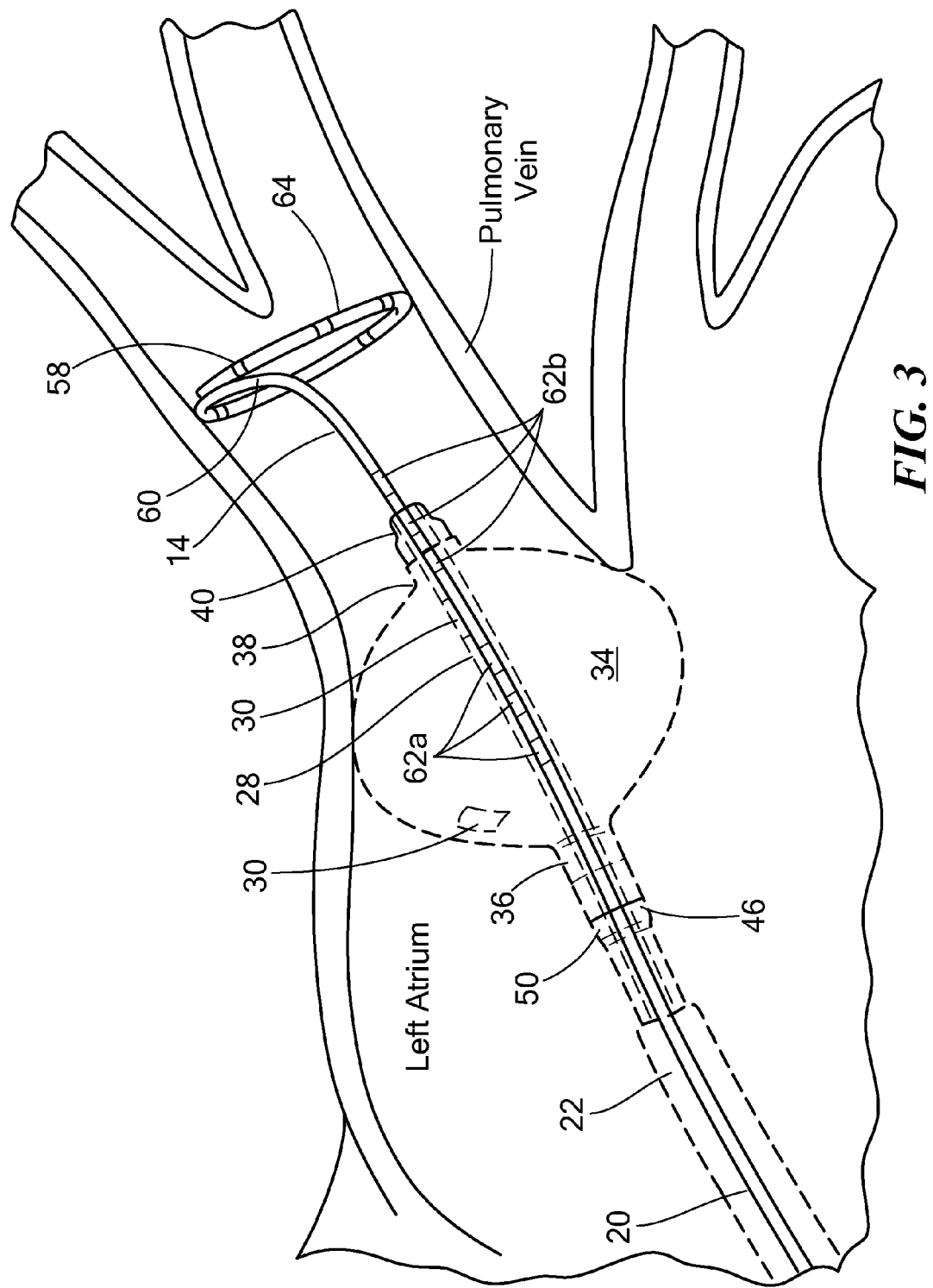
FIG. 3 shows an alternate view of the heatable mapping catheter within the exemplary cryotreatment catheter in the configuration of FIG. 2.
Figure 5:
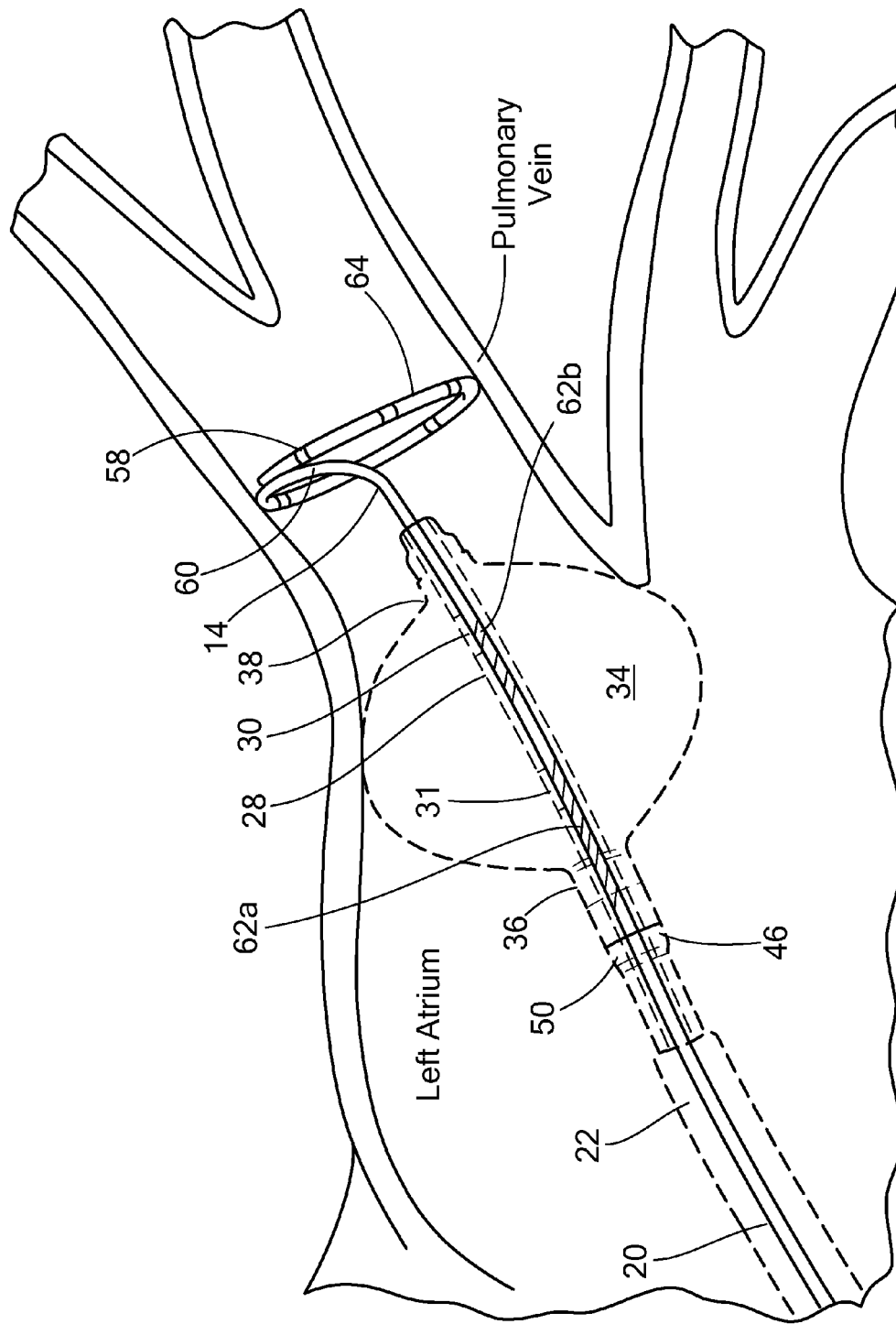
FIG. 5 shows an alternate view of the heatable mapping catheter within the exemplary cryotreatment catheter in the configuration of FIG. 4.

As shown in FIGS. 3 and 5, the mapping catheter 14 may include a plurality of heating elements 62 located on the mapping catheter 14 such that one or more heating elements are disposed within the guide wire lumen 28 proximate the cryoballoon 34 (that is, within the area of the guide wire lumen 28 most affected by the temperature of the cryoballoon 34) when the mapping catheter is extended (FIGS. 2 and 3) and when the mapping catheter 14 is retracted (FIGS. 4 and 5). For example, FIG. 3 shows a first set of heating elements 62a that is disposed within the cryoballoon 34 when the mapping catheter 14 is extended, and a second set of heating elements 62b that may be disposed within the cryoballoon 34 when the mapping catheter 14 is retracted. Depending on the position of the mapping catheter 14, either the first set 62a, second set 62b, or both sets of heating elements may selectively be activated. Further, an individual heating element 62 from either set may selectively be activated alone or in combination with other heating elements 62. As non-limiting examples, the one or more heating elements 62 may be electrodes to which radiofrequency energy is delivered, such as electrode bands (as shown in FIG. 3), or the one or more heating elements 62 may be flexible heating films or wires that can be wrapped around the mapping catheter 14 (as shown in FIG. 5). For example, the one or more heating elements 62 may be disposed on an outer surface of the mapping catheter 14 if they are composed of biocompatible materials (for example, if the one or more heating elements 62 are composed of metal such as platinum-iridium alloy, gold, or gold plated metals such as copper or stainless steel), or the one or more heating elements 62 be disposed or incorporated within the mapping catheter 14 if they are conductive and/or not biocompatible.

The one or more processors 70 may be in communication with the one or more temperature 30 and/or pressure 31 sensors, and programmable to activate the one or more heating elements 62 automatically when temperature signals sent from one or more temperature sensors 30 to the computer 66 indicate that freezing temperatures have been reached within the guide wire lumen 28 or are about to be reached. As a non-limiting example, one or more temperature sensors 30 may be positioned inside the guide wire lumen 28 (as shown in FIG. 3), inside the cryoballoon 34, such as in the proximal portion of the balloon, outside the cryoballoon, such as at the tissue-balloon interface, or within or on the distal portion 60 of the mapping catheter 14. For example, the one or more processors 70 may activate the one or more heating elements 62 when the temperature within the guide wire lumen is between approximately 0° C. and approximately −10° C., as sensed by one or more temperature sensors 30, such as those located within the guide wire lumen 28. Additionally or alternatively, the one or more processors 70 may activate the one or more heating elements 62 when one or more pressure sensors 31 indicate that liquid inside the guide wire lumen 28 has frozen (for example, if using the pressure wedge monitoring technique, disappearance of the pressure wave may indicate frozen fluid). As a non-limiting example, a pressure sensor 31 may be located on the mapping catheter 14 at a location on the mapping catheter 14 that would be within the guide wire lumen 28 at the onset of cryotreatment. FIG. 3 shows a pressure sensor 31 in such a location on the mapping catheter 14 having no heating elements. If the pressure sensor 31 is located on a mapping catheter 14 with heating elements, the pressure sensor 31 could be located, for example, proximal of one or more heating elements 62. At this location, the pressure sensor 31 may be able to sense the disappearance of pressure waves, which is an indicator of frozen liquid within the guide wire lumen 28. Additionally or alternatively, the one or more heating elements 62 may be manually activated based on, for example, temperature signals from the one or more temperature sensors 30 or time from initiation of cryotreatment. Whether activated manually or automatically, only the one or more heating elements 62 located within the guide wire lumen 28 proximate the cryoballoon 34 (that is, within the area of the guide wire lumen 28 most affected by the temperature of the cryoballoon 34) may be activated. Further, the portion of the guide wire lumen 28 proximate the cryoballoon may include an insulative layer 63 so that the heat generated by the one or more heating elements 62 will only affect the temperature of fluid within the guide wire lumen 28, with the warming effect within the guide wire lumen 28 being faster and more efficient, but will not affect the temperature of coolant circulating through the cryoballoon 34 and/or the temperature of the cryoballoon 34 itself (as shown in FIG. 2).

Figure 6:
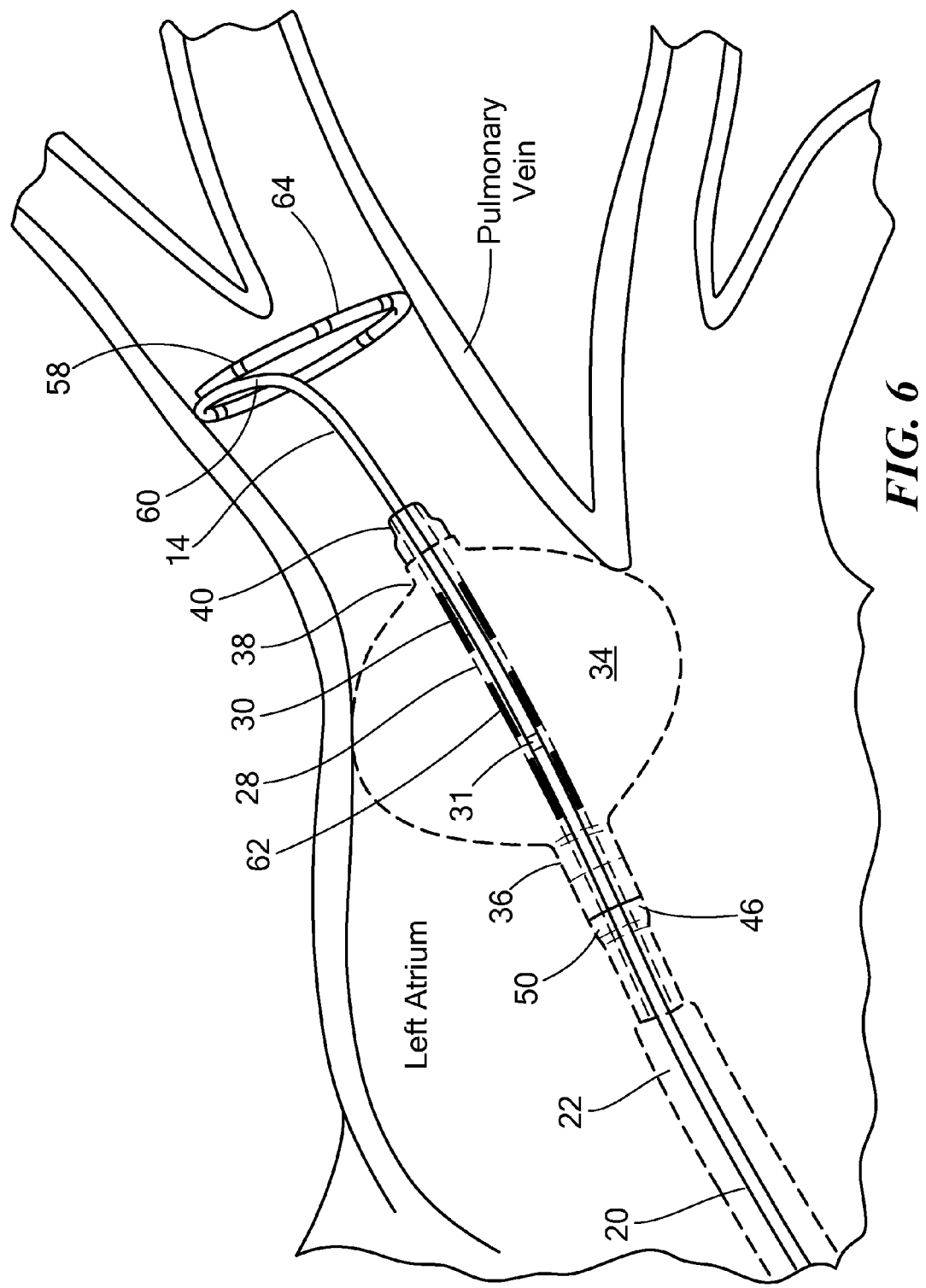
FIG. 6 shows a cryotreatment cryotreatment catheter having one or more heating elements within the guide wire lumen.

Referring now to FIG. 6, an alternative embodiment of a cryotreatment catheter is shown. As shown in FIG. 6, the cryotreatment catheter 12 may include one or more heating elements 62 disposed within the guide wire lumen 28 proximate the cryoballoon 34 (that is, in the area of the guide wire lumen 28 most affected by the temperature of the cryoballoon 34). Although six heating elements 62 are shown in FIG. 6, it will be understood that any number and/or configuration of heating elements 62 may be used. For example, the one or more heating elements 62 may be discrete, continuous, elongate, wound about an inner surface of the guide wire lumen 28, or the like. The one or more heating elements 62 may be electrodes (for example, radiofrequency electrodes), bands or areas of exposed conductive material, and/or conductive wires or braids affixed to an inner surface of the lumen and/or integrated within the guide wire lumen 28. In such an embodiment, the mapping catheter 14 may be without heating elements 62. Thus, fluid within the guide wire lumen 28 may be thawed or prevented from freezing by the one or more heating elements 62 regardless of the position of the mapping catheter 14 (that is, whether the mapping catheter 14 is extended, retracted, or in a position therebetween). It will be understood that one or more heating elements 62 may be included both on an inner surface of the guide wire lumen 28 (as shown in FIG. 6) and on the mapping catheter 14 (as shown in FIGS. 3 and 5). Such a configuration would enhance the heating potential and accelerate the melting process.

Figure 7:
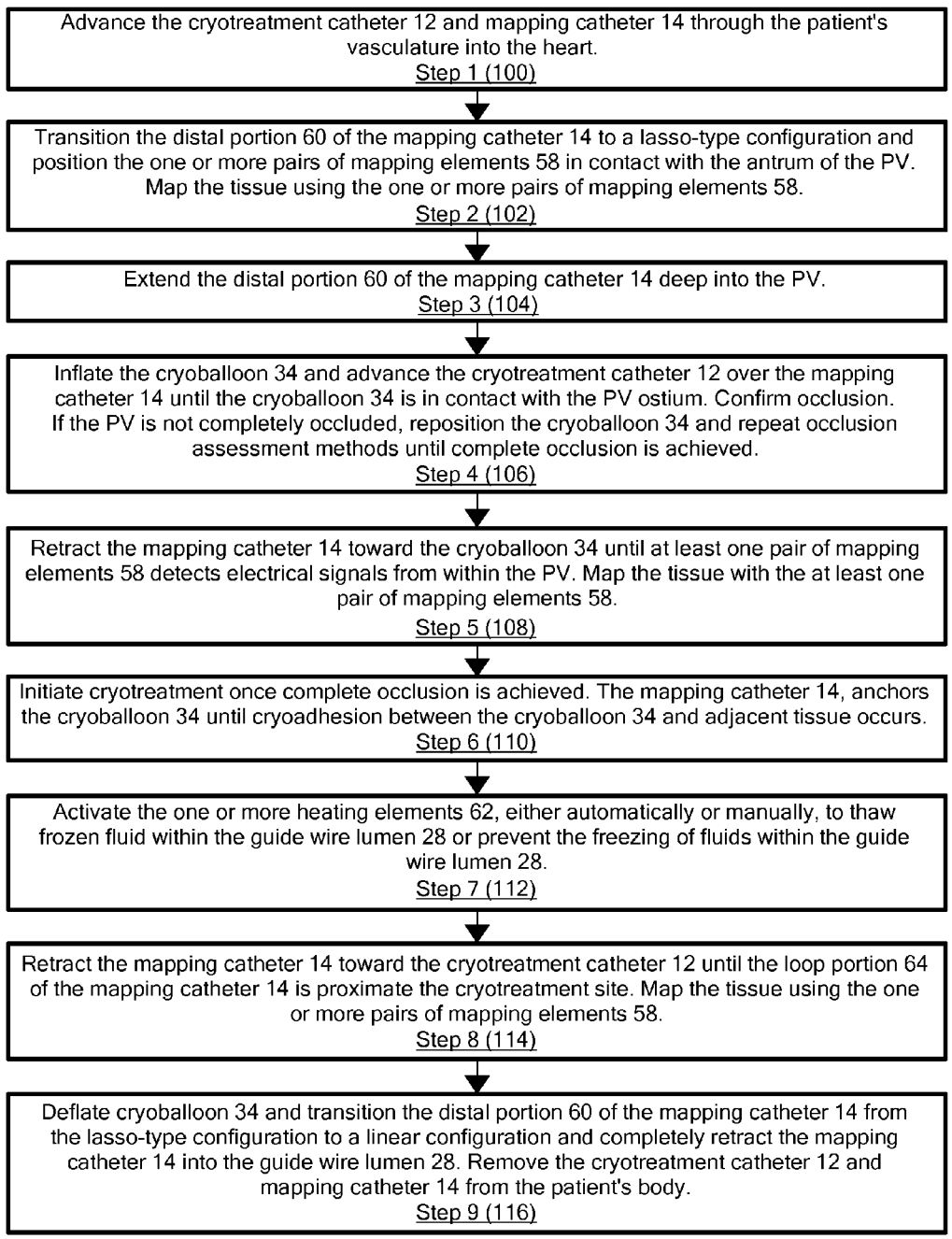
FIG. 7 shows a method of treating tissue using a cryotreatment system with one or more heating elements.

Referring now to FIG. 7, a method of treating tissue using a cryotreatment system with one or more heating elements is shown. In the first step 100 of the method, the cryotreatment catheter 12 and mapping catheter 14 may be advanced through the patient's vasculature into the heart (for example, the left atrium of the heart). In the second step 102 of the method, the distal portion 60 of the mapping catheter 14 may be transitioned to a lasso-type configuration and positioned such that at least one of the one or more pairs of mapping elements 58 are in contact with the PV antrum. Electrical signals in the tissue may be detected and recorded (that is, the tissue may be mapped), such as PV potentials. In the third step 104 of the method, the mapping catheter 14 may be advanced deep within a PV (referred to as being in the extended position). In this position, the mapping catheter 14 may anchor the cryotreatment device 12. For example, the distal portion 60 of the mapping catheter 14, the area on which the one or more pairs of mapping elements 58 may be disposed, may be manipulated and/or steered to assume a lasso-type configuration, such that the loop portion 64 is in contact with at least a portion of an inner circumference of the PV. Even though the one or more pairs of mapping elements 58 may be in contact with the PV tissue, electrical signals may be absent and, therefore, no recording may be performed in this step.

In the fourth step 106 of the method, the cryoballoon 34 may be inflated and the cryotreatment catheter 14 advanced over the mapping catheter 14 until the cryoballoon 34 is in contact with the PV ostium. Contrast medium with fluoroscopy and/or other methods such as pressure wedge monitoring may be used to confirm occlusion. If these methods indicate that the PV is not completely occluded, the cryoballoon 34 may be repositioned and the assessment methods repeated until complete occlusion is achieved. In the fifth step 108 of the method, the mapping catheter 14 may be partially retracted toward the cryoballoon 34 until at least one pair of mapping elements 58 detects electrical signals from within the PV. This position may also be referred to as an extended position, although the mapping catheter 14 is not extended as far within the PV as in the second step 102 of the method. Once electrical signals are detected, they may be recorded by the one or more pairs of mapping elements 58. If this retraction of the mapping catheter 14 causes the cryoballoon 34 to slip from the ostium and complete occlusion is lost, the mapping catheter 14 may be re-extended to position the distal portion 60 deeper within the PV. At this location, electrical signals may be lost (that is, not be present). However, it will be understood that this fifth step is optional. Rather, the distal portion 60 of the mapping catheter 14 may remain deep within the PV until after cryoadhesion occurs and the anchoring function of the mapping catheter 14 is less important. The mapping catheter 14 may be extended or retracted at any stage of cryotreatment because of the heat generated by the one or more heating elements 62.

In the sixth step 110 of the method, cryotreatment may be initiated once complete occlusion is achieved. For example, coolant may be circulated from the fluid supply reservoir 48 through the fluid flow paths of the system in order to cool the cryoballoon 34. In one embodiment, unexpanded coolant may pass from the fluid supply reservoir 48 through the fluid injection lumen 46 and into the cryoballoon 34. Although not shown, fluid may pass from the fluid injection lumen 46 into the cryoballoon 34 through a fluid injection element such as a nozzle, opening, or other component. After exiting the fluid injection element, the unexpanded coolant may expand and cool the cryoballoon 34 by the Joule-Thomson effect. Expanded coolant may then pass into the fluid recovery lumen 50 and either vented to the atmosphere, stored in the fluid recovery reservoir 52, or recirculated through the system 10. Fluid may be drawn into the fluid recovery lumen 50 from the cryoballoon 34 by a vacuum 54. The mapping catheter 14 may be left in the extended position during initiation of cryotreatment and used to anchor or otherwise offer support to the cryoballoon 34 until cryoadhesion between the cryoballoon 34 and adjacent tissue occurs.

In the seventh step 112 of the method, the one or more heating elements 62 may be activated, either automatically or manually. For example, readings from one or more sensors 30, such as temperature sensors and/or pressure sensors, may cause the one or more processors 70 to activate the one or more heating elements 62 automatically. Additionally or alternatively, readings from the one or more sensors 30, such as temperature or pressure measurements, may be shown on the display 68. The time elapsed since initiation of cryotreatment may also be displayed. Based on the displayed measurements, the user may activate one or more heating elements 62 either individually or in groups. As a non-limiting example, the heating elements 62 may be activated, either automatically or manually, when the temperature within the cryoballoon 34 or the guide wire lumen 28 reaches a threshold temperature (for example, when the temperature within the guide wire lumen 28 is approximately 0° C.±5° C. or at 10 seconds±5 seconds after commencement of cryotreatment.

In the eighth step 114 of the method, the mapping catheter 14 may be retracted toward the cryotreatment catheter 12 until the loop portion 64 of the mapping catheter 14 is proximate the cryotreatment site (but outside the guide wire lumen 28). It will be understood that the mapping catheter 14 may be retracted or extended by any amount in order to detect and record an additional set of PV potentials, and does not have to be retracted all the way to the cryotreatment site. Due to the warming effect of activation of the one or more heating elements 62, the mapping catheter 14 may be longitudinally movable in either direction in order to record additional electrical signals. Further, the sixth step 110 of the method may be repeated as many times as desired. Indeed, any of the method steps may be repeated as many times as is necessary to seat the cryoballoon 34 against the PV ostium, acquire adequate mapping data, and/or securely anchor the mapping catheter 14 and cryotreatment catheter 12 in position. As an example, following cryotreatment, the distal portion 60 of the mapping catheter 14 may be withdrawn from the PV and repositioned at the PV antrum (for example, the distal portion 60 may be in the lasso-type configuration and at least partially encircle the PV ostium) such that at least one pair of mapping elements 58 detects and records electrical signals from the PV antrum. This may allow for assessment of the effectiveness of the cryotreatment. Depending at least in part on the signals detected and recorded from the PV antrum, the cryotreatment device 12 may be used to retreat the same area of tissue or may be relocated to treat a different area of tissue. Cardiac issue, such as the PV antrum, may be mapped as many times and in as many locations as necessary to confirm that the cryotreatment was successful.

Optionally, at any step in the treatment method, one or more heating elements in the mapping catheter 14 distal portion may be activated to prevent ice formation and/or thaw ice that may have formed on one or more mapping elements 58 because of activation of the cryoballoon 34. This method is shown and described in more detail in FIGS. 8A-10.

In the ninth step 116 of the method, the cryoballoon 34 may be deflated and the distal portion 60 of the mapping catheter 14 may be transitioned from the lasso-type configuration to a linear configuration and completely retracted within the guide wire lumen 28. For example, the ninth step 116 may be performed once mapping has confirmed successful cryotreatment. The cryotreatment catheter 12, with the mapping catheter 14 therein, may then be removed from the patient's body. Alternatively, the mapping catheter 14 may be completely removed from the cryotreatment catheter 12 before the cryotreatment catheter 12 is removed from the patient's body.

Figure 8A:
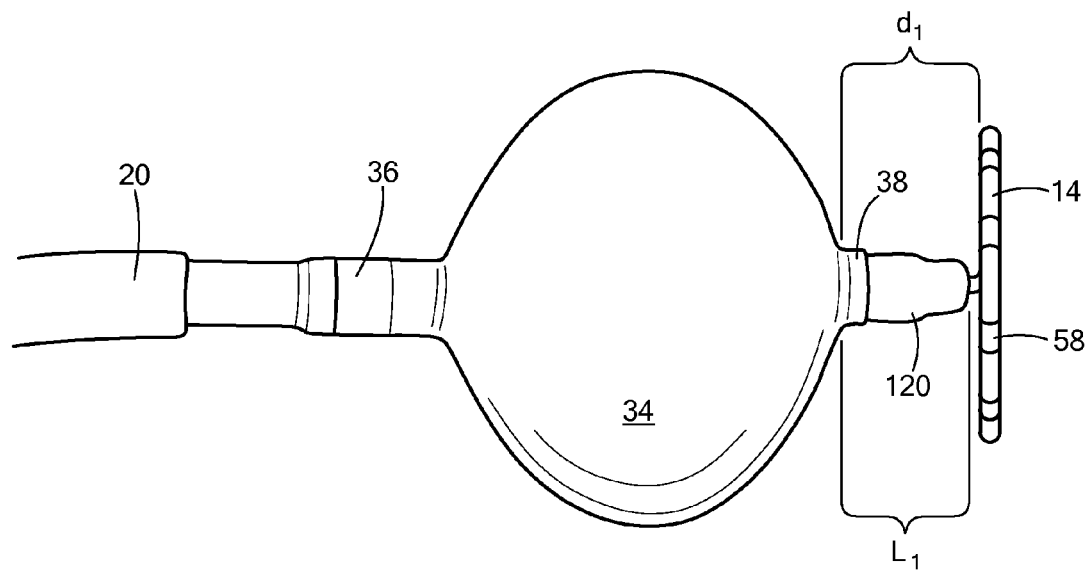
FIG. 8A shows a distal portion of a first exemplary cryotreatment catheter with mapping catheter.
Figure 8B:
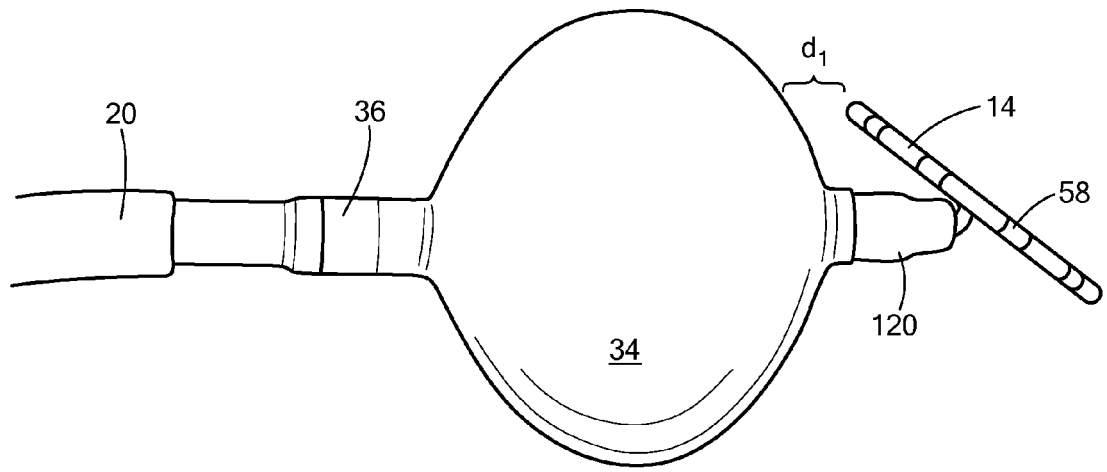
FIG. 8B shows a distal portion of an exemplary cryotreatment catheter with mapping catheter, the mapping catheter being prolapsed toward the cryoballoon of the cryotreatment catheter.
Figure 8C:
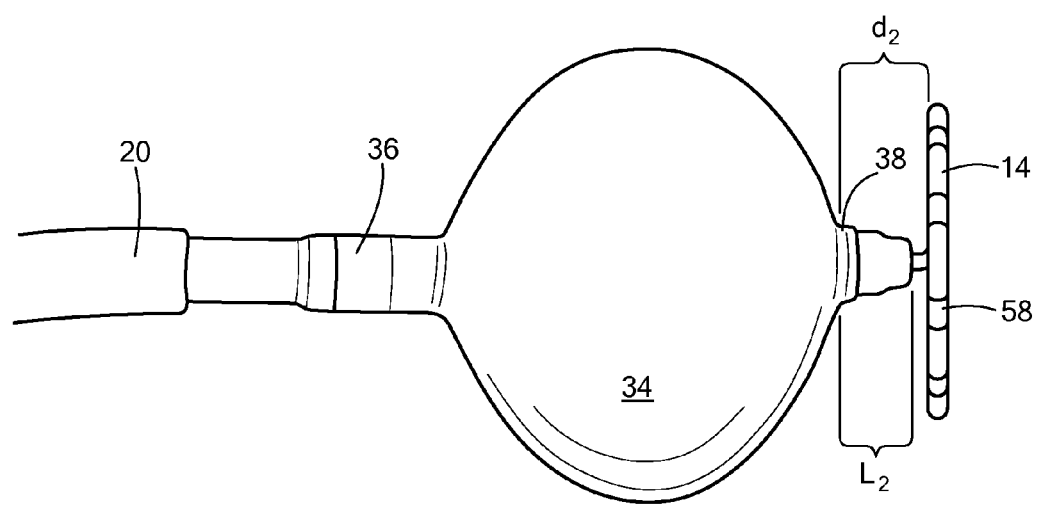
FIG. 8C shows a second exemplary cryotreatment catheter with a shortened distal tip.
Figure 8D:
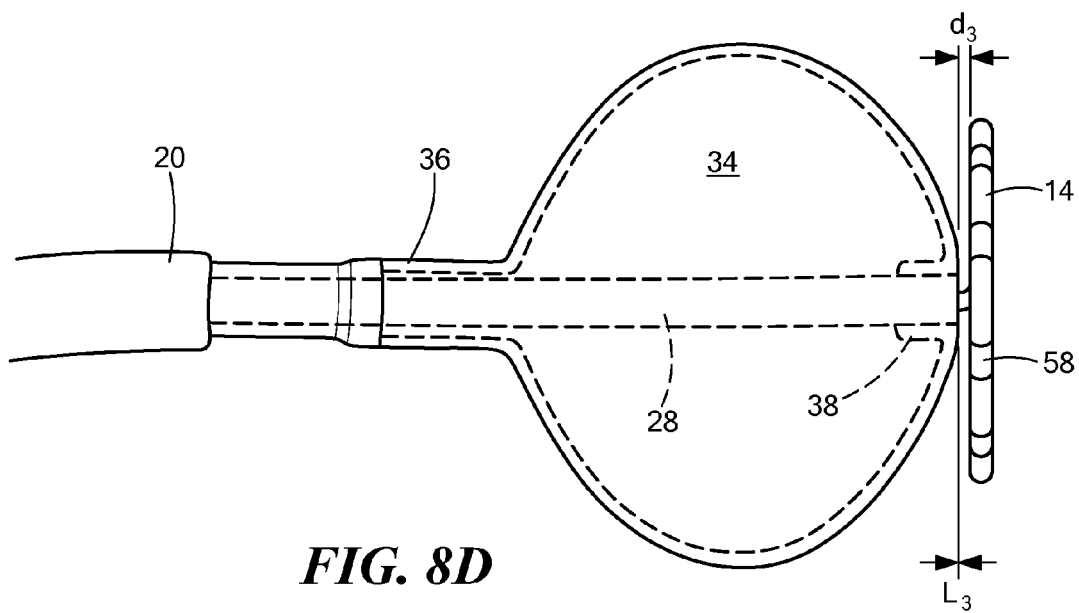
FIG. 8D shows a third exemplary cryotreatment catheter with a shortened distal tip.

Referring now to FIGS. 8A-8D, various cryotreatment catheter distal tips are shown. Although the devices shown in FIGS. 8A-8C are exemplary, they show a comparison between devices with a longer distal tip 120 (FIGS. 8A and 8B) and those having a reduced distal tip 120 (FIGS. 8C and 8D). As shown in FIGS. 8A and 8B, the device may have a distal tip 120 with length $L_1$. As shown in FIG. 8C, the cryotreatment catheter 12 may have a distal tip 120 with length $L_2$ or, as shown in FIG. 8D, a distal tip 120 with length $L_3$. For example, the distal tip 120 of the cryotreatment catheter 12 shown in FIG. 8C may be approximately half the length of that of FIGS. 8A and 8B. That is, $$L_2 \approx 0.5 \times L_1.$$

For example, $L_1$ may be between approximately 12 mm and approximately 13 mm, and $L_2$ may be approximately 6 mm. Further, the smallest possible distance $d_2$ between at least one of the mapping elements 58 and the cryoballoon 34 in FIG. 8C may be less than the smallest possible distance $d_1$ between at least one of the mapping elements 58 and the cryoballoon 34 in FIG. 8A when the mapping element 58 is in contact with target tissue and the loop portion 64 of the mapping catheter 14 is oriented in a plane that is substantially orthogonal to the longitudinal axis of the cryotreatment catheter 12 (for example, as shown in FIGS. 8A, 8C, and 8D). $L_3$ may be even shorter than $L_2$, allowing the mapping catheter 14 to be placed as close as possible to the cryoballoon 34. $L_3$ may approach a length of 0 mm and the smallest possible distance $d_3$ between at least one of the mapping elements 58 and the cryoballoon 34 may be smaller than both $d_1$ and $_2$ when the mapping element 58 is in contact with target tissue. To achieve this, the distal portion or neck 38 of the cryoballoon 34 may be turned inward, within the expansion chamber 122 of the cryoballoon 34, and affixed (for example, chemically bonded, thermally bonded, or otherwise adhered) to an external surface of the guidewire lumen 28 (as shown in FIG. 8D). Alternatively, the distal portion or neck 38 of the cryoballoon 34 may be turned inward, within the guidewire lumen 28, and affixed to an internal surface of the guidewire lumen 28 (not shown). In these embodiments with a distal tip length being approximately 0 mm, the cryoballoon 34 may define a distal face that is coterminous with the guidewire lumen 28 (as shown in FIG. 8D).

Additionally, as shown in FIG. 8B, the loop portion 64 may become prolapsed, that is, angled toward the cryoballoon 34. This may occur if the inner diameter of the vein or other anatomical feature being treated is less than the outer diameter of the loop portion 64, thereby forcing a part of the loop portion 64, and one or more mapping elements 58, to be very close to or even in contact with the cryoballoon 34, depending on the length of the distal tip 120. That is, the distance d between at least one of the mapping elements 58 and the cryoballoon 34 may be approximately 0 mm. This, in turn, may make those mapping elements 58 more vulnerable to ice formation. One or more heating elements 62 may be selectively activated to heat those mapping elements 58 closest to the cryoballoon 34 and not other mapping elements 58. Alternatively, all mapping elements 58 may be activated if required, based on signals from one or more temperature sensors 126 and/or visual feedback. Although the loop portion 64 is shown in a prolapsed position in association with the device of FIG. 8A, it will be understood that the loop portion 64 may also become prolapsed when used with cryotreatment devices having reduced distal tips (as shown in FIGS. 8C and 8D).

Figure 9:
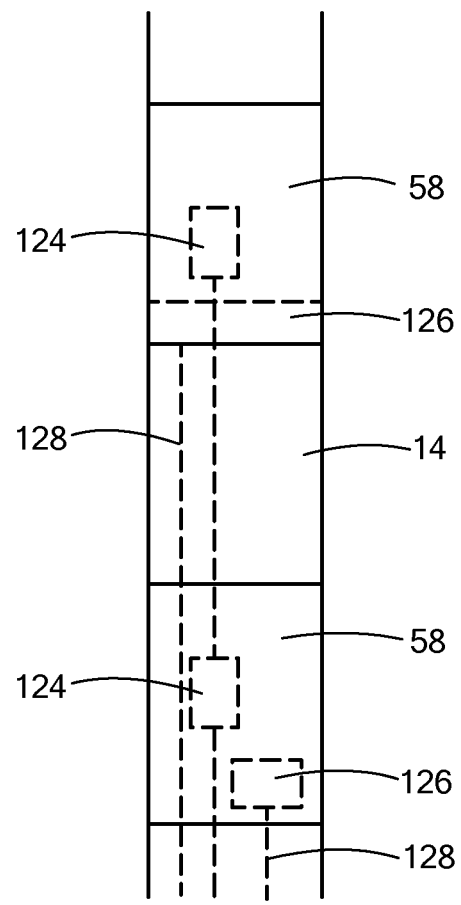
FIG. 9 shows a close-up view of a mapping element having a temperature sensor.

The closer the mapping elements 58 are to the cryoballoon 34, the better the chance of detecting and recording PVPs from pulmonary vein tissue (that is, detecting and recording PVPs from tissue within the pulmonary vein that may conduct electrical signals). Further, positioning the mapping elements 58 close to the cryoballoon 34 may provide more accurate feedback about the cryoablation or cryotreatment procedure, such as time to effect of electrical isolation of the pulmonary vein. However, the low temperatures reached by the cryoballoon may cause the formation of ice on the mapping catheter 14 and mapping elements 58 when the mapping elements 58 are located proximate the cryoballoon 34. This may cause a loss of signal, and thus negate the benefits of mapping element placement. To avoid this effect, each mapping element 58 may include an electrode heating element 124, as shown in FIG. 9. The mapping element 58 shown in FIG. 9 may also include a temperature sensor 126. Additionally or alternatively, the cryotreatment catheter 12 may include one or more temperature sensors 126 located, for example, within the cryoballoon 34, on an outer surface of the cryoballoon 34, and/or on the distal tip 120 (as shown in FIG. 10).

In the embodiment shown in FIG. 9, a temperature sensor 126 may be coupled to, affixed to, integrated with, or otherwise in communication with each mapping element 58. Both the temperature sensor 126 and the mapping element 58 may be band shaped (as shown in the upper portion of FIG. 9), or the temperature sensor 126 may be a discrete conductive area (as shown in the lower portion of FIG. 9). However, it will be understood that the temperature sensor 126 may have any suitable size, shape, or configuration, including a configuration wherein the temperature sensor 126 is a wire wrapped around a portion of or in communication with the mapping element 58. The temperature sensor 126 may be in communication with the console, directly or indirectly, through one or more wires 128. Each mapping element 58 may be in communication with the energy generator 56, such as a radiofrequency generator. Energy, such as radiofrequency energy, may be transmitted to the mapping element 58 through one or more wires 128 disposed within the mapping catheter 14. When the temperature sensor 126 detects a local temperature of, for example, approximately 0° C. or below, the temperature sensor 126 may transmit a signal to the console 16 (for example, the one or more processors 70) and the console 16 may automatically activate and/or adjust the energy generator 56 to transmit non-ablative energy to the mapping element 58 in response to the received signal, the amount (for example, voltage and/or duration) of which energy being sufficient to thaw ice on or prevent the freezing of the mapping element 58 without damaging adjacent tissue or interfering with the mapping element's ability to record electrograms. Additionally or alternatively, measured temperatures may be displayed to the user, and the user may manually selectively activate one or more heating elements, or all heating elements, or may override or adjust the console's automatic activation of the heating elements.

Each mapping electrode 58 may continue to record electrograms during a period of increased energy delivery, such as when energy is delivered to the mapping element 58 to thaw ice on the mapping element 58. Further, each of the mapping elements 58 may be individually monitored and energy may be selectively delivered to one or more of the mapping elements 58. As a non-limiting example, the one or more processors 70 may be programmed or programmable to execute one or more algorithms for receiving and interpreting temperature signal data (for example, data received from the one or more temperature sensors 126) and determining a predicted temperature at each mapping element 58. The one or more processors 70 may then communicate an appropriate energy delivery scheme to each mapping element 58 based at least in part on the predicted temperature and/or received signals. This energy may be sufficient to melt or prevent the formation of ice on the mapping element 58, but may not be enough to damage or thermally affect adjacent tissue. Alternatively, the one or more processors 70 may interpret the temperature signal from the temperature sensor 126 and generate a display to alert the user and/or an audible or visual alarm. The user may then manually activate and/or adjust the energy generator 56 to transmit non-ablative energy to the heating element 124. Likewise, the energy delivery may be terminated or reduced, either automatically or manually as described, if the temperature sensor 126 records a temperature above approximately 0° C. As a non-limiting example, the energy delivery may be terminated or reduced if the temperature sensor 126 measures a temperature at the mapping element 58 of about approximately 5° C.±1° C.

Figure 10:
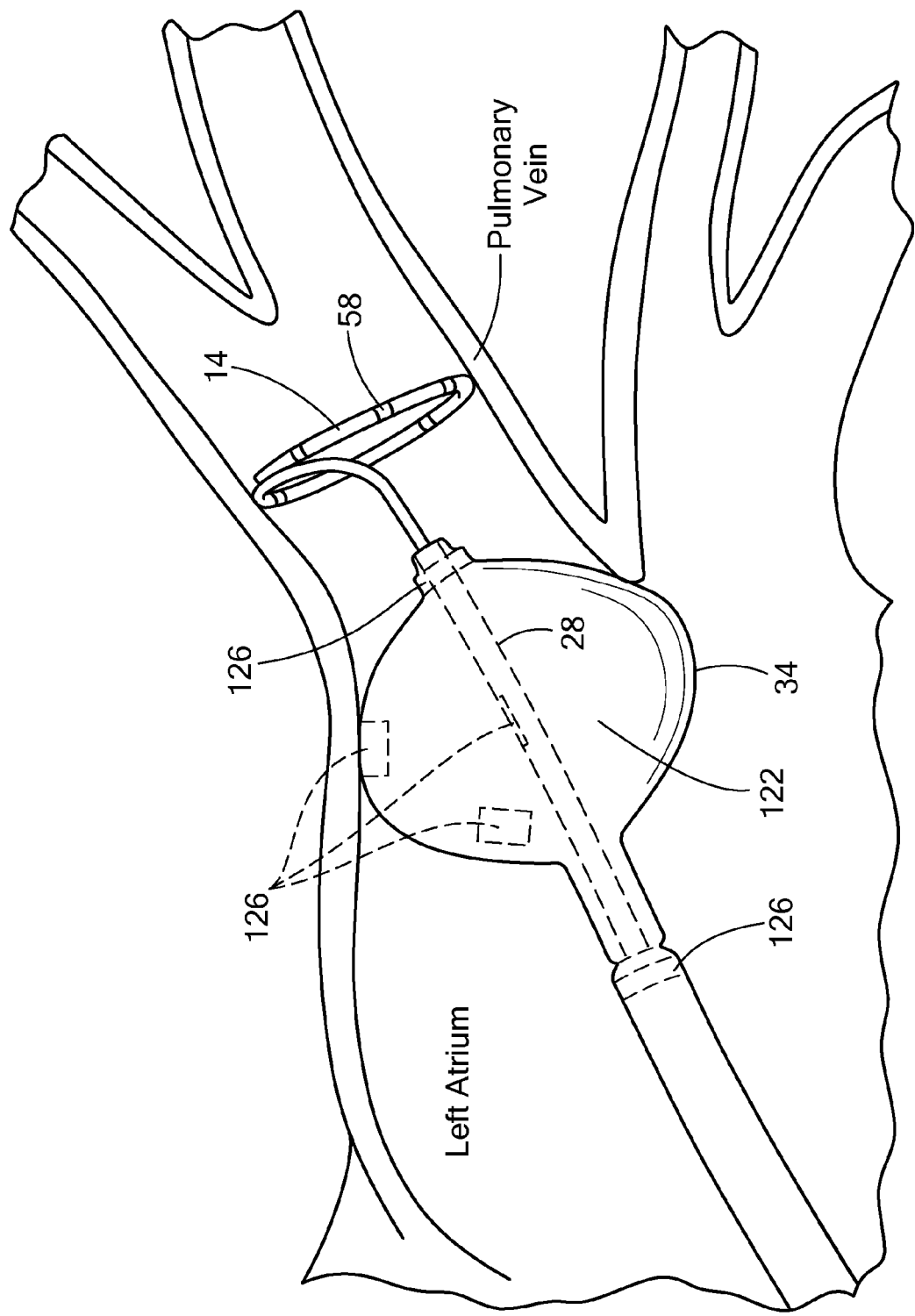
FIG. 10 shows a view of a cryotreatment catheter having one or more temperature sensors.

The cryotreatment catheter 12 shown in FIG. 10 may operate using generally the same principles as that of FIG. 9; however, the catheter 12 of FIG. 10 may include one or more temperature sensors 126 at locations other than the mapping elements 58. The temperature sensors 126 may be coupled to, affixed to, integrated with, or otherwise attached to various portions of the catheter 12. As shown, temperature sensors 126 may be located within the cryoballoon 34 (for example, within the expansion chamber 122, either on an internal surface of the cryoballoon 34 or the guidewire lumen 28), on an outer surface of the cryoballoon 34 (such as at a location that will be in contact with the target tissue), on the distal tip 120, or on the elongate body 20. Additionally or alternatively, temperature sensors 126 may be located at other areas, such as within the fluid injection lumen and/or within the fluid recovery lumen. Further, it will be understood that one or more temperature sensors 126 may also be located on the mapping catheter, as shown in FIG. 9. In much the same way as in the embodiment of FIG. 9, the one or more temperature sensors 126 may transmit temperature signals to the console 16, which may then automatically activate and/or adjust the transmission of energy, such as radiofrequency energy, from the energy generator 56 to the mapping elements 58 in response to the received temperature signals. Further, each of the mapping elements 58 may be individually monitored and energy may be selectively delivered to one or more of the mapping elements 58. As a non-limiting example, the one or more processors 70 may be programmed or programmable to execute one or more algorithms for receiving and interpreting temperature signal data and determining a predicted temperature at each mapping element 58. The one or more processors 70 may then communicate an appropriate energy delivery scheme to each mapping element 58 based at least in part on the predicted temperature and/or received signals. For example, the one or more processors 70 may initiate the transmission of energy to each mapping element 58 for which the processors 70 have predicted a temperature of approximately 0° C. or below. Additionally or alternatively, the one or more processors 70 may instruct the console 16 to generate a display to alert the user and/or an audible or visual alarm. The user may then manually activate and/or adjust the energy generator 56 to transmit non-ablative energy to the heating element 124. Likewise, the energy delivery may be terminated or reduced, either automatically or manually as described, if the temperature sensor 126 records a temperature above approximately 0° C. As a non-limiting example, the energy delivery may be terminated or reduced if the temperature sensor 126 measures a temperature at the mapping element 58 of about approximately 5° C.±1° C.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A system for mapping electrical signals within myocardial tissue, the system comprising:
   one or more mapping electrodes on a mapping catheter;
   an energy source in communication with each of the one or more of the mapping electrodes; and
   a processor in communication with one or more temperature sensors, the processor being configured to control the energy source to deliver non-ablative energy to the one or more mapping electrodes when the processor determines that the temperature of the one or more mapping electrodes is below a threshold temperature, the determination being based at least in part on temperature signals received from the one or more temperature sensors.

2. The system of claim 1, further comprising a treatment catheter including an expandable element and an elongate body including a lumen, the mapping catheter being slidably disposed within the lumen of the treatment catheter elongate body.

3. The system of claim 2, wherein the one or more mapping elements are in direct communication with the one or more temperature sensors.

4. The system of claim 3, wherein each of the one or more mapping elements includes at least one of the one or more temperature sensors.

5. The system of claim 2, wherein the treatment catheter includes a distal tip located distal of the expandable element.

6. The system of claim 5, wherein at least one of the one or more temperature sensors is located on the treatment catheter distal tip.

7. The system of claim 5, wherein the treatment catheter distal tip has a length of between approximately 0.01 mm and approximately 13 mm.

8. The system of claim 7, wherein the treatment catheter distal tip has a length of between approximately 0.01 mm and approximately 1 mm.

9. The system of claim 8, wherein the treatment catheter further includes a guidewire lumen, the expandable element includes a proximal neck and a distal neck, and the distal neck is turned inward and coupled to a distal portion of the guidewire lumen within the cryoballoon, the expandable element defining a distal face that is coterminous with the guidewire lumen.

10. The system of claim 7, wherein at least one of the one or more mapping electrodes is positionable between 0 mm and 2 mm of the expandable element when the at least one mapping electrode is mapping electrical signals within myocardial tissue.

11. The system of claim 2, wherein at least one of the one or more temperature sensors is located on the treatment catheter.

12. The system of claim 11, wherein at least one of the one or more temperature sensors is located on an outer surface of the expandable element.

13. The system of claim 11, wherein at least one of the one or more temperature sensors is located on an inner surface of the expandable element.

14. The system of claim 2, wherein the expandable element is in fluid communication with a source of coolant.

15. The system of claim 1, wherein the threshold temperature is approximately 0° C.

16. A cryotreatment system comprising:
   a cryotreatment device including a first elongate body and a cryoballoon, the first elongate body including a guide wire lumen;
   a mapping device including a second elongate body, the second elongate body being disposable within the guide wire lumen of the first elongate body;
   a plurality of mapping elements on a distal portion of the second elongate body;
   a plurality of temperature sensors on at least one of the cryotreatment device and the mapping device;
   a radiofrequency energy generator in communication with the plurality of mapping elements; and
   a processor in communication with the plurality of temperature sensors and the radiofrequency energy generator, the processor being configured to control the energy generator to deliver non-ablative energy to the plurality of mapping elements when the processor determines that a temperature of at least one of the plurality of mapping elements is approximately 0° C., the determination being based at least in part on temperature signals received from the plurality of temperature sensors.

17. The system of claim 16, wherein the cryotreatment device further includes a distal tip.

18. The system of claim 17, wherein at least one of the plurality of mapping elements is positionable within approximately 3 mm of the cryoballoon when at least one of the plurality of mapping elements is in contact with an area of target tissue.

19. The system of claim 16, the distal tip defining a length of between approximately 0.01 mm and approximately 3 mm.

* * * * *